US00PP29744P2

(12) United States Plant Patent
Probst

(10) Patent No.: US PP29,744 P2
(45) Date of Patent: Oct. 9, 2018

(54) ***EPIMEDIUM* PLANT NAMED 'NINJA STARS'**

(50) Latin Name: ***Epimedium* sp. nov.**
Varietal Denomination: Ninja Stars

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 15/530,961

(22) Filed: Mar. 29, 2017

(51) Int. Cl.
*A01H 5/02* (2018.01)

(52) U.S. Cl.
USPC ..... Plt./429

(58) Field of Classification Search
USPC ..... Plt./429
See application file for complete search history.

(56) References Cited

PUBLICATIONS http://dev.sunnyborder.com/ Jul. 5, 2014.*

* cited by examiner

*Primary Examiner* — Annette H Para
(74) *Attorney, Agent, or Firm* — Penny J. Aguirre

(57) ABSTRACT

A new cultivar of *Epimedium* hybrid, 'Ninja Stars', characterized by its leaves that are long, narrow, and evergreen with very spiny leaf margins, its foliage that emerges bronze in color in spring and turns medium dark green and semi-glossy in appearance as the season progresses, its numerous erect flower stems held above the foliage that are large in size and yellow in color, semi-long rhizomes averaging 10 cm in length, and its cold hardiness to at least U.S.D.A. Zone 4.

2 Drawing Sheets

Botanical classification: *Epimedium* sp. nov.
Cultivar designation: 'Ninja Stars'.

BACKGROUND OF THE INVENTION

The present invention relates to a new and distinct cultivar of *Epimedium* plant of hybrid origin, botanically known as *Epimedium* 'Ninja Stars' and will be referred to hereafter by its cultivar name, 'Ninja Stars'.

The new invention arose from an ongoing controlled breeding program in Hubbardston, Mass. The objective of the breeding program is to develop hybrid cultivars of *Epimedium* with unique and superior garden attributes. In particular, to develop cultivars with long, narrow evergreen leaves, large flowers held above the foliage, semi-spreading rhizomes for the ease of propagation and cold hardiness at least to U.S.D.A. Zone 5.

The Inventor made a controlled cross in March of 2013 in his test garden in Hubbardston, Mass. between *Epimedium* sp. nov. 'Spine Tingler' (not patented), as the female parent and an unnamed and unpatented plant of *Epimedium* sp. nov. from his proprietary breeding program as the male parent. 'Ninja Stars' was selected in May of 2006 as a single unique plant amongst the resulting seedlings. *Epimedium* sp. nov is a species collected by the Inventor in China and is currently considered new to science and awaiting confirmation by a taxonomist.

Asexual propagation of the new cultivar was first accomplished by rhizome division in Hubbardston, Mass. in July of 2006 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of 'Ninja Stars'. These attributes in combination distinguish 'Ninja Stars' as a new and distinct cultivar of *Epimedium*.

1. 'Ninja Stars' exhibits leaves that are long, narrow, and evergreen with very spiny leaf margins.
2. 'Ninja Stars' exhibits foliage that emerges bronze in color in spring and turns medium dark green and semi-glossy in appearance as the season progresses.
3. 'Ninja Stars' exhibits numerous erect flower stems held above the foliage with flowers that are large in size and yellow in color.
4. 'Ninja Stars' exhibits semi-long rhizomes averaging 10 cm in length.
5. 'Ninja Stars' exhibits a cold hardiness to at least U.S.D.A. Zone 4.

The female parent of 'Ninja Stars', 'Spine Tingler', differs from 'Ninja Stars' in having leaves and flowers that are smaller in size, and rhizomes that are very short and clump-type. The male parent of 'Ninja Stars' differs in having foliage that is larger in size and rhizomes that are much longer. 'Ninja Stars' can be compared to the *Epimedium* cultivars 'Amber Queen' (U.S. Plant Pat. No. 17,197) and 'Fire Dragon' (U.S. Plant Pat. No. 17,179). 'Amber Queen' is similar to 'Ninja Stars' in height and in having evergreen foliage. 'Amber Queen' differs from 'Ninja Stars' in having inflorescences that are amber orange in color, in having short, clumping type rhizomes and in having proportionately wider foliage compared to its length. 'Fire Dragon' is similar to 'Ninja Stars' in having petals that are yellow in color, evergreen foliage and rhizomes that are semi-spreading. 'Fire Dragon' differs from 'Ninja Stars' in having sepals that are pink in color, panicles that are shorter in length with fewer flowers per panicle, a much shorter plant habit and leaflets that are smaller in size and proportionately wider compared to their length.

BRIEF DESCRIPTION OF THE DRAWINGS

The accompanying colored photographs illustrate the overall appearance and distinct characteristics of the new

*Epimedium*. The photographs were taken of a two year-old plant of 'Ninja Stars' as grown outdoors in a 2-gallon container in Kensington, Conn.

Figure 1:
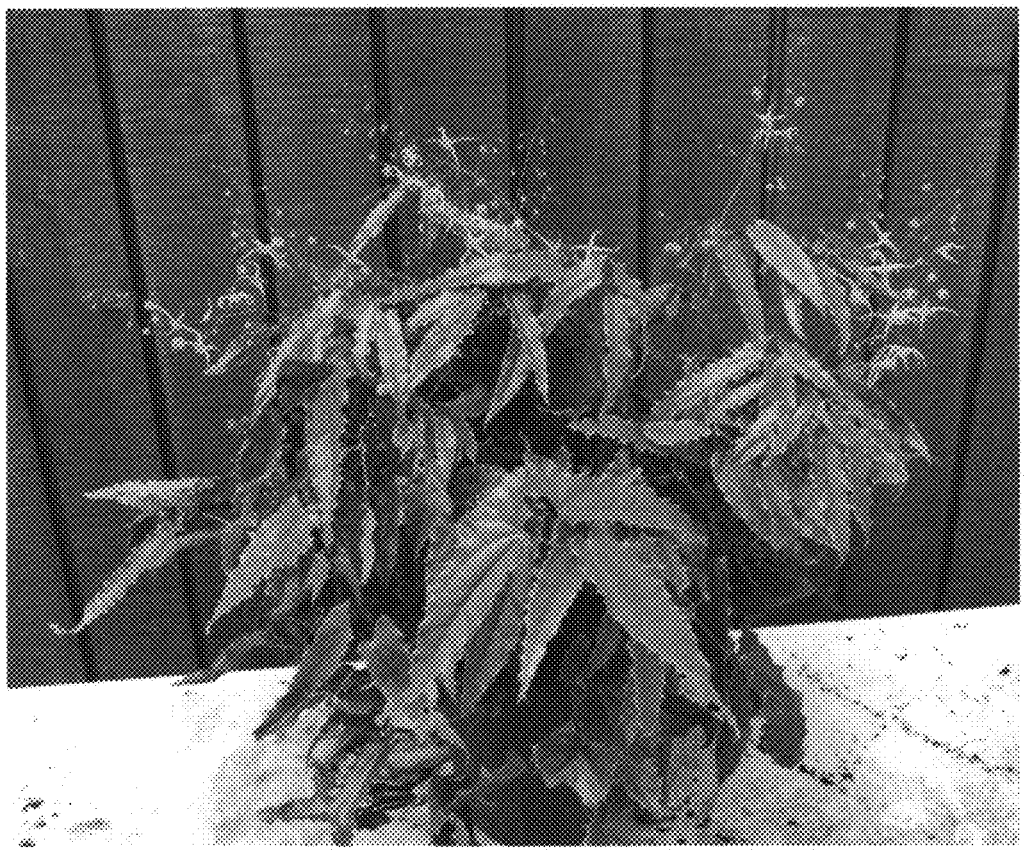

The photograph in FIG. 1 provides a side view of 'Ninja Stars' in bloom and shows the new foliage over the lower one year-old evergreen foliage.

Figure 2:
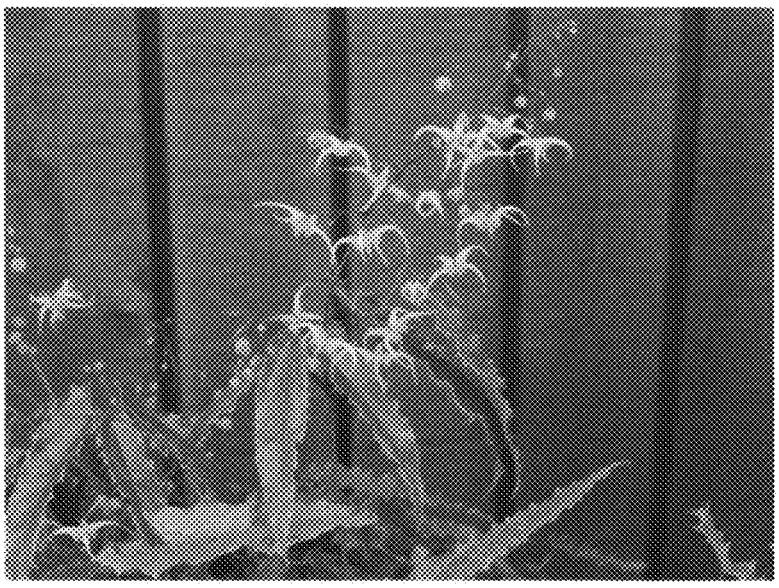

The photograph in FIG. 2 provides a view of an inflorescence of 'Ninja Stars'.

Figure 3:
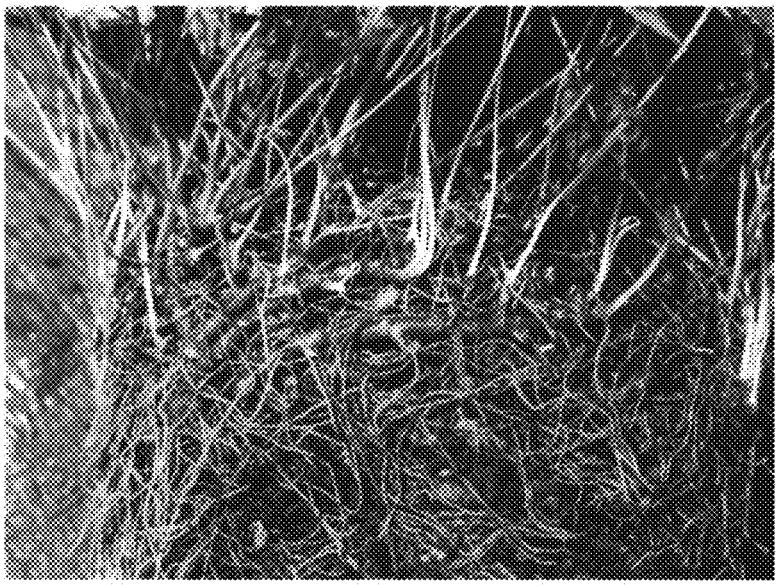

The photograph in FIG. 3 provides a close-up view of the rhizomes of 'Ninja Stars'.

The colors in the photographs are as close as possible with the digital photography and printing techniques utilized and the color codes in the detailed botanical description more accurately describe the colors of the new *Epimedium*.

DETAILED BOTANICAL DESCRIPTION OF THE PLANT

The following is a detailed description of one year-old plants as grown outdoors in 2-quart containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Plant habit*.—Upright, and spreading with semi-long rhizomes.

*Plant type*.—Herbaceous perennial.

*Blooming period*.—Early May to mid June in Hubbardston, Mass.

*Plant height and spread*.—40 to 50 cm in height and up to 60 cm in width on a 3-year plant in the landscape.

*Diseases resistance*.—No susceptibility or resistance to diseases has been observed.

*Root description*.—Dense, fibrous roots on rhizomes.

*Rhizomes*.—166A and 178A in color, an average of 5 cm in length and 2 cm in width as grown in a 2-qt pot and an average of 10 cm in length and 2 cm in width as grown in a 2-gallon container.

*Hardiness*.—At least in U.S.D.A. Zones 4 to 8.

*Branching habit*.—Branches arise from rhizome.

*Propagation*.—Rhizome division.

*Growth rate*.—Vigorous, rhizomes growth averages 5 cm a year.

Stem description (flowering stem):

*Stem size*.—An average of 25 cm in length (to base of inflorescence) and 2 mm in width.

*Stem color*.—165A.

*Stem surface*.—Glabrous.

Foliage description:

*Leaf division*.—Compound, ternate.

*Leaf size*.—An average of 15 cm in width and 10 cm in length.

*Leaf number*.—2 per flowering stem.

*Leaflet shape*.—Lanceolate.

*Leaflet margins*.—Serrate with sharp spines; an average of 2.5 mm in length and 166B in color.

*Leaflet size*.—An average of 9 cm in length and 2 cm in width.

*Leaflet apex*.—Acuminate.

*Leaflet base*.—Terminal leaflet cordate (with lobes acute), lateral leaves asymmetric (with lobes acute).

*Leaflet surface*.—New foliage; upper surface glabrous and glossy, lower surface glabrous and dull, mature foliage; upper surface glabrous and semi glossy, lower surface glabrous and dull.

*Leaf arrangement*.—Opposite.

*Leaflet venation*.—Odd pinnate and palmate near base, not conspicuous, mid rib on upper and lower surface 161A in color.

*Leaflet aspect*.—Slightly concave when mature on upper surface.

*Leaflet color*.—New foliage upper and lower surface; 138A and strongly suffused with 166A; mature upper surface (evergreen); 137A; mature lower surface; 138A (evergreen).

*Leaf attachment*.—On petioles that arise from rhizome.

*Petioles*.—An average of 15 cm in length and 1 mm in width on basal leaves, an average 6 cm in length and 1 mm in width on flowering stem leaves, of 165A in color, glabrous surface.

*Petiolules*.—An average of 2 cm in length on terminal leaf and 7 mm in length on lateral leaves, 1 mm in diameter, surface glabrous, color 161A and can be suffused slightly with 166A.

Inflorescence description:

*Inflorescence type*.—Compound raceme with branches typically 3-flowered toward base (corymb) with single flowers toward apex.

*Inflorescence size*.—Average of 6.5 cm in length (from base of raceme) and 3 cm in width.

*Number of blooms per raceme*.—An average of 24.

*Flower buds*.—Globose in shape, about 3.5 mm in length and 2 mm in width, N144A in color.

*Flower size*.—An average of 4 cm in diameter and 1 cm in depth.

*Flower fragrance*.—None.

*Lastingness of flowers*.—About 5 days, dependent on weather.

*Sepals*.—4, elliptic in shape, broadly cuneate base, acute to slightly acuminate apex, larger flowers; 4.5 mm in length, 2.2 mm in width, and 145B in color on both surfaces, smaller flowers; 4 mm in length, 2 mm in width, and 144B in color on both surfaces, glabrous on upper and lower surfaces.

*Petals*.—4, 2 cm in length, 2 mm in width at base and 4 mm in depth, base is truncate, spur portion is 1.5 cm in length, slightly recurved, with apex narrowing to a fine point, all surfaces are glabrous, lamina portion is an average of 5 mm in depth, color of all surfaces 3A.

*Pedicel*.—An average of 1 cm in length on terminal flowers and 7 mm in length on lateral flowers, very fine (>1 mm in width) and wiry, surface is glandular (more prominent near base of flower), color 144A and suffused with 165A.

*Rachis* (*peduncle*).—An average of 13 cm in length and 1 mm in width, branches for cormbs are an average of 1.5 cm in length and <1 mm in with, color 144A and slightly suffused with 165A.

*Androecium*.—4 stamens, filaments 4 mm in length and 154C in color, anthers 0.7 mm in length with abundant pollen about 13C in color.

*Gynoecium*.—1 pistil, filament 2.5 mm in length and 159C in color, stigma <1 mm in length and 145D in color, ovary is oblong in shape, 3 mm in length and 145D in color.

*Fruit/seeds*.—Fruit: a thin walled capsule, 2-valved, an average of 2 cm in length at maturity, seeds; an average of 12 to 15 seeds per capsule.

It is claimed:

1. A new and distinct cultivar of *Epimedium* plant named 'Ninja Stars' as herein illustrated and described.

* * * * *